United States Patent [19]
Coonrod et al.

[11] Patent Number: 6,146,884
[45] Date of Patent: Nov. 14, 2000

[54] APPARATUS FOR THE PREPARATION OF MULTIPLE POLLEN SAMPLES FOR CRYOGENIC PRESERVATION

[75] Inventors: Daren K. Coonrod, Fort Collins, Colo.; Norman P. Cloud, Pleasanton, Tex.; John A. Greaves, Ankeny, Iowa; Raymond R. Russotti, Tyngsboro, Mass.

[73] Assignee: Garst Seed Company, Slater, Iowa

[21] Appl. No.: 09/375,101

[22] Filed: Aug. 16, 1999

Related U.S. Application Data

[63] Continuation-in-part of application No. 09/166,047, Oct. 5, 1998, abandoned.
[51] Int. Cl.[7] .................................................... C12M 1/00
[52] U.S. Cl. .................................. 435/307.1; 435/286.6; 34/402; 47/58; 426/419; 426/465
[58] Field of Search ........................... 422/40; 435/284.1, 435/286.6, 307.1; 34/402, 406, 408; 47/58; 426/419, 465

[56] References Cited

U.S. PATENT DOCUMENTS

| | | |
|---|---|---|
| 3,986,521 | 10/1976 | Wittmann-Liebold et al. . |
| 4,746,071 | 5/1988 | Grunhoff et al. . |
| 5,233,844 | 8/1993 | Knippscheer et al. . |
| 5,433,020 | 7/1995 | Leech, Jr. . |
| 5,596,838 | 1/1997 | Greaves et al. . |
| 5,689,914 | 11/1997 | Greaves et al. . |
| 5,694,700 | 12/1997 | Greaves et al. . |

OTHER PUBLICATIONS

Seery, T., Designer Seeds Delight Farmers, Denver Post, Sep. 14, 1997.

Barnabas, B., Kovacs, G., Abranyi, A., & Pfahler, P., Effects of Pollen Storage by Drying and Deep–Freezing on the Expression of Different Agronomic Traits in Maize (*Zea mays* L.), 39 Euphytica 221 (1988).

Collins, T.C., Lertmongkol, V., & Jones, J.P., Pollen Storage of Certain Agronomic Species in Liquid Air, 13 Crop Sci. 493 (1973).

Barnabas, B., Preservation of Maize Pollen, 25 Biotechnology in Agriculture and Forestry 607, in Maize (Y.P.S. Bajaj ed., 1994).

Barnabas, B., Effect of Water Loss on Germination Ability of Maize (*Zea mays* L.) Pollen, 55 Annals of Botany 201 (1985).

Barnabas, B. & Rajki, E., Fertility of Deep–frozen Maize (*Zea Mays* L.) Pollen, Annals of Botany (1981).

Barnabas, B., & Rajki, E., Storage of Maize (*Zea Mays* L.) Pollen at –196 degrees Celsius in Liqud Nitrogen , 25 Euphytica 747 (1976).

(List continued on next page.)

*Primary Examiner*—David A. Redding
*Attorney, Agent, or Firm*—Daniel A. Rosenberg; Kent A. Herink; Davis Brown Law Firm

[57] ABSTRACT

An apparatus for the preparation of multiple pollen samples for cryogenic preservation comprising a plurality of chambers for the storage of pollen samples. A vacuum pump reduces the pressure within the interior of the chambers through a vacuum manifold that operatively connects with the pollen samples in the interior of the chambers. An air source vents the interior of the chambers to atmospheric pressure through an air manifold operatively connected with the pollen samples in the interior of the chambers. A vacuum controller controls the pressure within the interior of the chambers through operative connections to the vacuum manifold, the air manifold, the air source, and the vacuum pump. The vacuum controller pulses the pressure with the interior of the chambers between a first and a second reduced pressure level. A sensor operatively connected to the chambers senses the moisture content of the pollen samples within the interior of the chambers at the reduced pressure levels. After the pollen samples reach a predetermined moisture content, the pollen samples can be cyrogenically preserved in a pollen bank for later plant-breeding use.

23 Claims, 11 Drawing Sheets

OTHER PUBLICATIONS

Nath, J. & Anderson, J.O., Effects of Freezing–Drying on Viability and Storage of *Lilium Longiflorum* L. and *Zea mays* L. Pollen, 12 Cryobiology 81 (1975).

Daniel, L., Retention of the Germinating Power of Pollen during Storage, Institute of Genetics of the Hungarian–Academy of Sciences (Hungary) (abstract).

Connor, K. & Towill, L., Pollen–handling Protocol and Hydration/Dehydration Characteristics of Pollen for Application to Long–Term Storage, Kluwer Acad. Publ. at 77 (1993).

Walden, D.B., Male Gametophyte of *Zea mays* L., 7 Crop Sci. 441 (1967).

Shands, H.L., Janisch, D.C., & Dickson, A.D., Germination Response of Barley Following Different Harvesting Conditions and Storage Treatments, 7 Crop Sci. 444 (1967) (abstract).

Barnabas, B. & Fridivalszky, L., Adhesion and Germination of Differently Treated Maize Pollen Grains on the Stigma, 30 Acta Botanica Hungarica 329 (1984).

Dereuddre, J., Blandin, S. & Hassen, N., Resistance of Alginate–Coated Somatic Embryos of Carrot (*Daucus–Coarota* L.) to Desiccation and Freezing in Liqud–Nitrogen—Effects of Preculture, 12 Cyro–Letters 125 (1991) (France) (abstract).

Dereuddree, J. & Gazeau, C., Natural Frost Resistance in Plants, Bull. De La Societe Bontanique De France, 133 Actualites Botaniques 7 (1986) (France) (abstract).

Dereuddre, J., Scottez, C., Arnaud, Y. & Duron, M., Resistance of Alginate–Coated Axillary Shoot Tips of Pear Tree (*Pyrus Communis* L. CV Beurre Hardy) in Vitro Plantlets to Dehydration and Subsequent Freezing in Liquid Nitrogen: Effects of Previous Cold Hardening—Shoot Tip Encapsulation in Calcium Alginate Bead; Cryopreservation and Plant Propagation; Germplasm Preservation, 3 Seances Acad. Sci. 320 (1990) (France) (abstract).

Morisset, C., Gazeau, C., Hansz, J. & Derruddre, J., Importance of Actin Cytoskeleton Behaviour During Preservation of Carrot Cell–Suspensions in Liquid–Nitrogen, 173 Protoplasm 35 (1993) (France) (abstract).

Nirde, P., Delbos, M. & Combes, D., New Procedure for Storing Pollen at Low Temperatures, 26 Plant Phys. & Biochem. 211 (1988) (France) (abstract).-

APPARATUS FOR THE PREPARATION OF MULTIPLE POLLEN SAMPLES FOR CRYOGENIC PRESERVATION

RELATED APPLICATIONS

The present application is a continuation-in-part of U.S. patent application Ser. No. 09/166,047 filed on Oct. 5, 1998 now abandoned.

BACKGROUND OF THE INVENTION

1. Field of Invention

The present invention relates to an apparatus for the preparation of multiple pollen samples for cryogenic preservation used in development of a pollen bank for plant-breeding purposes. More specifically, the invention relates to an apparatus that applies a vacuum to multiple storage units in a manner that allows for the controlled reduction of the moisture content of a pollen sample, thereby enabling cryogenic preservation of the pollen sample in a viable state for subsequent use for plant breeding.

2. Background of the Related Art

Plant breeding is one of the oldest recorded accomplishments of mankind. The ability to breed plants is an important mark in man's movement from nomadic life to organized society. Today's food crops are essentially the result of mankind's primitive plant-breeding attempts.

The practice of breeding has progressed to a science. Plant breeding became a science when genetic principles gave predictability to plant breeding. Plant breeding is basically man's conscious selection of genetic material instead of nature's selection of genetic material. The success of modern plant-breeding efforts include, for example, the increased productivity of field crops, the development of insect-resistant crops, and the development of disease-resistant crops. Numerous natural factors, however, create obstacles to plant-breeding efforts. These factors include the length of time necessary for development of a plant to its sexual maturity, the length of time to pollen viability, and the length of time to maturity of the pollen receptor. Presently, pollination can only occur when a plant is sexually mature, pollen is viable, and pollen receptors are available. In the case of inbreeding, the timing of these events does not normally create an obstacle to pollination. In hybrid breeding, however, specifically in plants such as maize, the timing of these events creates substantial obstacles to successful plant breeding. Cross pollination, where the pollen of one plant is used to pollinate a second plant requires precise timing. In other words, to successfully cross pollinate two plants, both plants much reach sexual maturity at the same time, pollen of the first plant must be viable, and the pollen receptors of the second plant must be available. The timing of these events, otherwise known as hitting the nick, comprises the rate limiting step in the cross pollination process. This requires careful timing of the maturity of both of the plants, and places severe limits on the physical proximity of the various plants.

One proposed method of solving these problems consists of developing a system of storing pollen in a viable condition in a pollen bank. This eliminates the need to coordinate the timing of sexual maturity of the two plants, and effectively eliminates the problem of requiring close physical proximity of the two plants. An effective method for the long-term storage of large quantities of viable pollen represents a significant advance in plant-breeding efforts. Furthermore, the long-term storage of viable pollen provides a unique ability to conserve and manipulate genetic resources. The ability to retrieve viable pollen, obtained from an individual plant stored for long periods of time, would provide great flexibility in plant-breeding programs. In today's present environment of plant-breeding research, a pollen storage system provides a method to expand molecular marker assisted breeding and transgenic biotechnology breeding programs by creating a germplasm bank of pollen for fingerprinting genetic material for future use in plant-breeding programs.

Methods for storage of viable pollen have been tested with some positive results. The success of these methods, however, varies dramatically based on the plant type involved. For example, maize traditionally is very desiccation sensitive, and also temperature sensitive. Freezing maize pollen directly, by exposure to liquid nitrogen, will completely destroy pollen viability. Other plant types do not exhibit this trait, however, the sensitivity to this type of treatment in many other plants is simply not known at this time. Research on maize pollen storage has shown some limited success using air flotation when large quantities of pollen are stored. An air flotation method of drying prepares maize pollen for medium to long-term storage. The system is somewhat limited as it does not allow the stored pollen to be readily used in commercial plant-breeding programs. The air flotation dries large quantities of pollen for storage. This stored pollen often exhibits less than acceptable levels of viability when employed. This makes the use of stored pollen on a commercial basis unsatisfactory.

U.S. Pat. No. 5,596,838, issued Jan. 28, 1997 and U.S. Pat. No. 5,689,914, issued Nov. 25, 1997, hereby incorporated by reference, disclose methods and apparatuses which enable the cryogenic preservation of pollen and, in particular, maize pollen. These systems involve apparatuses with only one pollen sample chamber, and which utilize manual control of the pressure within the chamber. Such an approach, while effective on a small scale, does not easily adopt to the preparation and preservation of multiple pollen samples on an automatic basis. Accordingly, a need still exists for the preservation and storage of pollen on a scale large enough to support modem research and commercial plant-breeding programs.

SUMMARY OF THE INVENTION

An object of the present invention comprises providing an apparatus for the preparation of multiple pollen samples for cryogenic preservation.

These and other objects of the present invention will become apparent to those skilled in the art upon reference to the following specification, drawings, and claims.

The present invention intends to overcome the difficulties encountered heretofore. To that end, the invention comprises an apparatus for the preparation of multiple pollen samples for cryogenic preservation comprising a plurality of chambers for the storage of pollen samples. A vacuum pump reduces the pressure within the interior of the chambers through a vacuum manifold operatively connects with the pollen samples in the interior of the chambers. An air source vents the interior of the chambers to atmospheric pressure through an air manifold operatively connected with the pollen samples in the interior of the chambers. A vacuum controller controls the pressure within the interior of the chambers through operative connections to the vacuum manifold, the air manifold, the air source, and the vacuum pump. The vacuum controller pulses the pressure within the interior of the chambers between a first and a second reduced pressure level. A sensor operatively connected to the chambers senses the moisture content of the pollen samples within the interior of the chambers at the reduced pressure levels.

DETAILED DESCRIPTION OF THE INVENTION

The detailed description of the preferred embodiment of the present invention relates to an apparatus for the preparation of multiple pollen samples for cryogenic preservation. This apparatus is particularly useful for the preparation and cryogenic preservation of maize pollen. It is anticipated, however, that the apparatus of the present invention with slight modifications can preserve the pollen of other plant types. For example, while the correlation to viability and desiccation of barley and wheat pollen is not as well understood as maize, it is anticipated that since barley and wheat are in the same family as maize, they should behave similarly. Additionally, the techniques of the present invention should adapt to sorghum. Furthermore, the apparatus of the present invention may prove useful to preserve germplasm, seed, ovum, and other biological materials without undue experimentation. The apparatus removes excess water from pollen samples by vacuum induced evaporation. At the correct level of dryness, i.e. removing excess water from the pollen to a predetermined moisture content level, allows exposing the pollen to temperatures in the range of minus 196° C. while maintaining a substantial level of viability after thawing the pollen sample. In other words, after the pollen sample is prepared, frozen, and stored, the pollen can be rapidly thawed and rehydrated for use in pollination. Such a technique allows gathering pollen samples from a wide array of plant types and geographical locations, without consideration to the time of season for later use in pollinating plants at any time and at any place. The apparatus of the present invention, therefore, eliminates the problems associated with hitting the nick, and by preserving multiple samples of pollen the apparatus for the first time facilitates large-scale pollination efforts.

Figure 1:
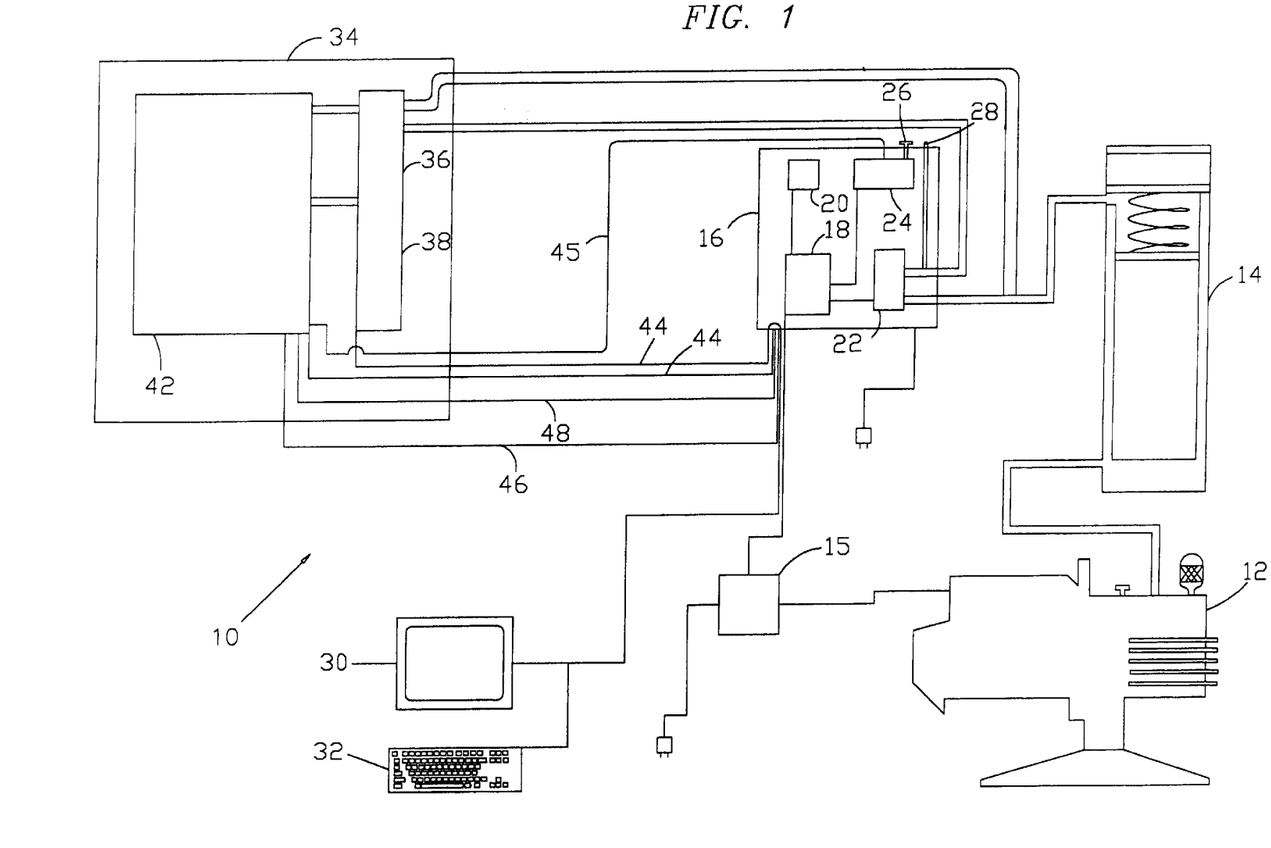
FIG. 1 is a block diagram of a pollen preservation apparatus.

In the Figures, FIG. 1 shows a pollen preparation apparatus shown generally at 10. The pollen preparation apparatus 10 comprises a central controller 16, which controls the operation of the apparatus 10. The central controller 16 functions in a manner similar to a general-purpose computer, with the addition of certain specialized components required to perform the function of the present invention. The central controller 16 links to a display terminal 30 and a keyboard 32 to enable the central controller 16 to receive input information from, and display output information to, an operator. The central controller 16 includes a power supply 20, a vacuum controller 22, and an oscillation controller 24. A PC controller 18 performs the function of a general-purpose computer. The PC controller 18 controls the various components of the central controller 16 and therefore, the pollen preparation apparatus 10, through computer program software means (not shown). This provides for fully automatic operation of the pollen preparation apparatus 10. It will be understood by those of ordinary skill in the art that the computer program software means residing in the PC controller 18 comprises the intelligent means for controlling and performing the various tasks described herein. The central controller 16 further comprises an oscillation amplitude manual adjustment dial 26 operatively connected to the oscillation controller 24, and an air source 28 operatively connected to the vacuum controller 22.

The pollen preparation apparatus 10 also includes a vacuum pump 12 operatively connected to the central controller 16 via a vacuum pump power supply 15. A desiccator 14 lies between the vacuum pump 12 and the central controller 16, and vacuum lines link the desiccator 14 to the vacuum pump 12 and to the central controller 16. In particular, the vacuum line linking the desiccator 14 and the central controller 16 operatively communicates with the vacuum controller 22. The pollen preparation apparatus 10 also features a chamber pad 34. Located within the chamber pad 34 are a plurality of chambers 42 (shown in detail in FIG. 4) for the placement of pollen samples, air manifold 36, and vacuum manifold 38. The components of the chamber pad 34 operatively communicate with the central controller 16 through a plurality of communication lines. In particular, the plurality of chambers 42 communicate with the central controller 16 via communication lines 44 and 46. The air manifold 36 and vacuum manifold 38 communicate with the central controller 16 through communication lines 44. The plurality of chambers 42 also communicate with the central controller 16 through oscillation communication line 45 and sensor communication line 48 (the operations of which will be described in further detail hereinafter).

Figure 2:
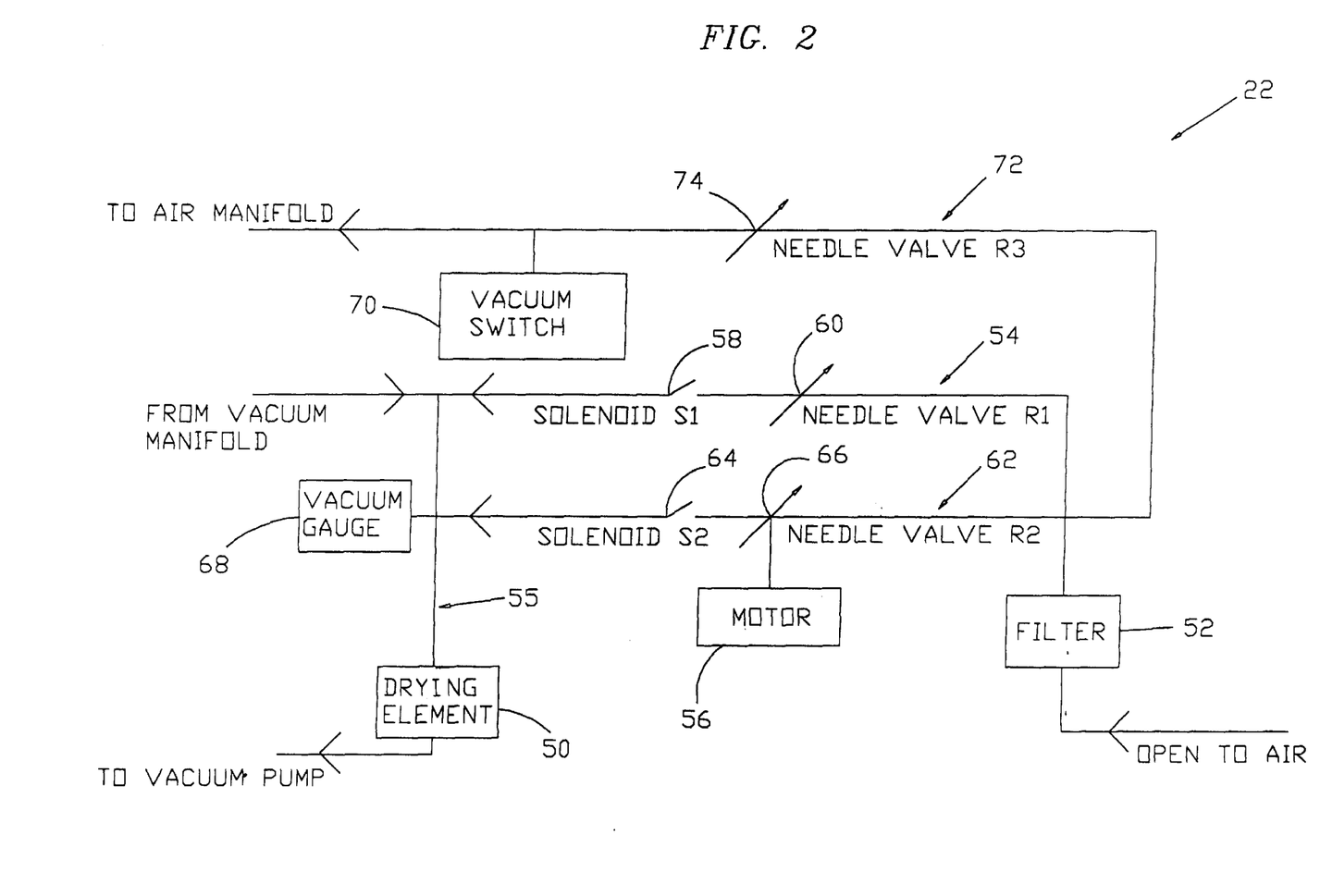
FIG. 2 is a block diagram of a vacuum controller of the pollen preservation apparatus of FIG. 1.

FIG. 2 shows schematically the configuration of the vacuum controller 22. The vacuum controller 22 includes a vacuum path 55 for airflow communication between the vacuum pump 12 and the vacuum manifold 38. Additionally, the vacuum path 55 includes a vacuum gauge 68 for monitoring the pressure within the vacuum path 55. The pressure registered on the vacuum gauge 68 is communicated back to the central controller 16. The vacuum controller 22 further comprises a first and a second vacuum manifold paths 54, 62. The first vacuum manifold path 54 comprises a first solenoid 58 located in series with, a first valve 60, the vacuum manifold 38, and the air source 28. The first vacuum manifold path 54 provides for boosted regulation of air flow between the air source 28 and vacuum manifold 38. The second vacuum manifold path 62, parallel to the first vacuum manifold path 54, comprises a vacuum control motor 56 located in the series with a second solenoid 64, a second valve 66, the vacuum manifold 38, and the air source 28. The vacuum control motor 56 through operative communication with the central controller 16 varies the position of the second valve 66 thereby regulating the air flow between the air source 28 and the vacuum manifold 38. This second solenoid 64 opens and closes air flow along the second manifold path 62. The vacuum controller 22 also includes an air manifold path 72, which includes a third valve 74 for regulating the air flow between the air source 28 and the air manifold 36. The third valve 74 can comprise a standard needle valve, or in the preferred embodiment of the present invention, the third valve 74 comprises a simple restriction plate. The third valve 74 serves merely to insure a vent rate to the chambers 42 that will not dislodge the pollen from the sample receptor 122.

Additionally, the vacuum controller 22 includes a drying element 50 and a filter 52. The drying element is located between the vacuum pump 12 and the vacuum manifold 38, along the vacuum path 55. The filter 52 is located along the path of the air source 28, and filters out particulate matter to avoid contamination of the chambers 42. The drying element 50 serves to control the moisture content of the vacuum pump 12, since evaporation coming from the pollen samples in the chambers 42 adds moisture to the air in the vacuum lines. Both the first and second solenoids 58, 64 include LEDs that light to indicate the status of the solenoids 58, 64. Finally, the vacuum controller 22 includes a vacuum switch 70 located along the air manifold path 72.

Figure 3:
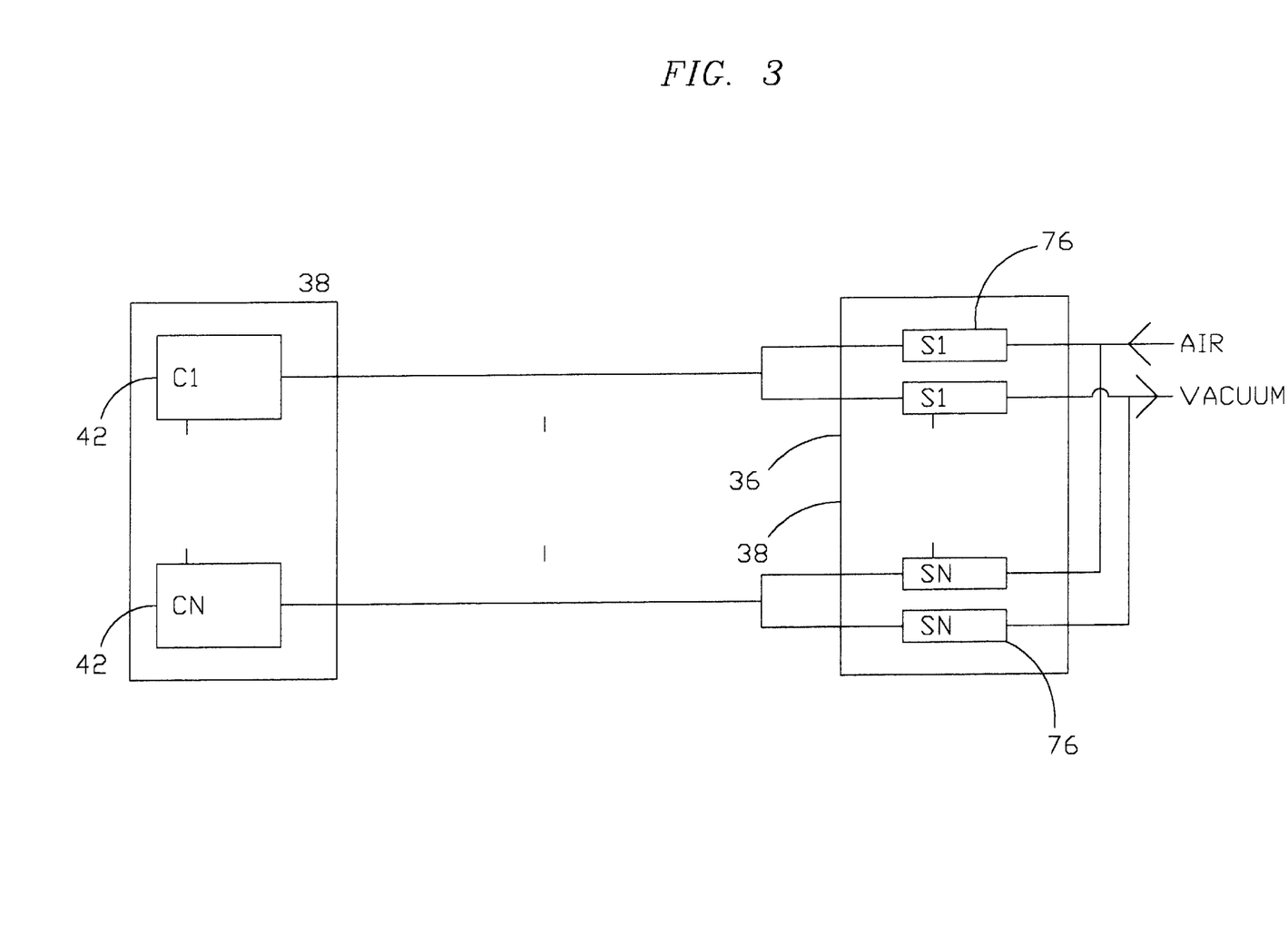
FIG. 3 is a block diagram of a vacuum manifold and a chamber pad of the pollen preservation apparatus of FIG. 1.

FIG. 3 shows the configuration of the plurality of chambers 42, air manifold 36, and vacuum manifold 38. The preferred embodiment of the present invention includes twenty-four chambers 42, however, those of ordinary skill in the art will appreciate the fact that the number of chambers 42 can vary without departing from the intended scope of the invention. The air manifold 36 and the vacuum manifold 38, while physically located together in the preferred embodiment of the invention, differ in that they comprise the separate collective vacuum and air paths between the vacuum controller 22 and the plurality of chambers 42. The present invention allows for individual control of each of the plurality of chambers 42, which is accomplished with two chamber solenoids 76 for each of the plurality of chambers 42. One of the pair of chamber solenoids 76 opens and closes to allow air flow between one of the plurality of chambers 42 and the first and second vacuum manifold paths 54, 62. The second of the pair of chamber solenoids 76 opens and closes air flow between one of the plurality of chambers 42 and the air manifold path 72. Each chamber solenoid 76 includes an LED that lights to indicate the status of the solenoid 76. In this manner, the air manifold 36 comprises all of the chamber solenoids 76 which control the communication of air flow between the plurality of chambers 42 and the air manifold path 72. In a similar fashion, the vacuum manifold 38 comprises all the chamber solenoids 76 which control the air flow between the plurality of chambers 42 and the first and second vacuum manifold paths 54, 62.

Figure 10:
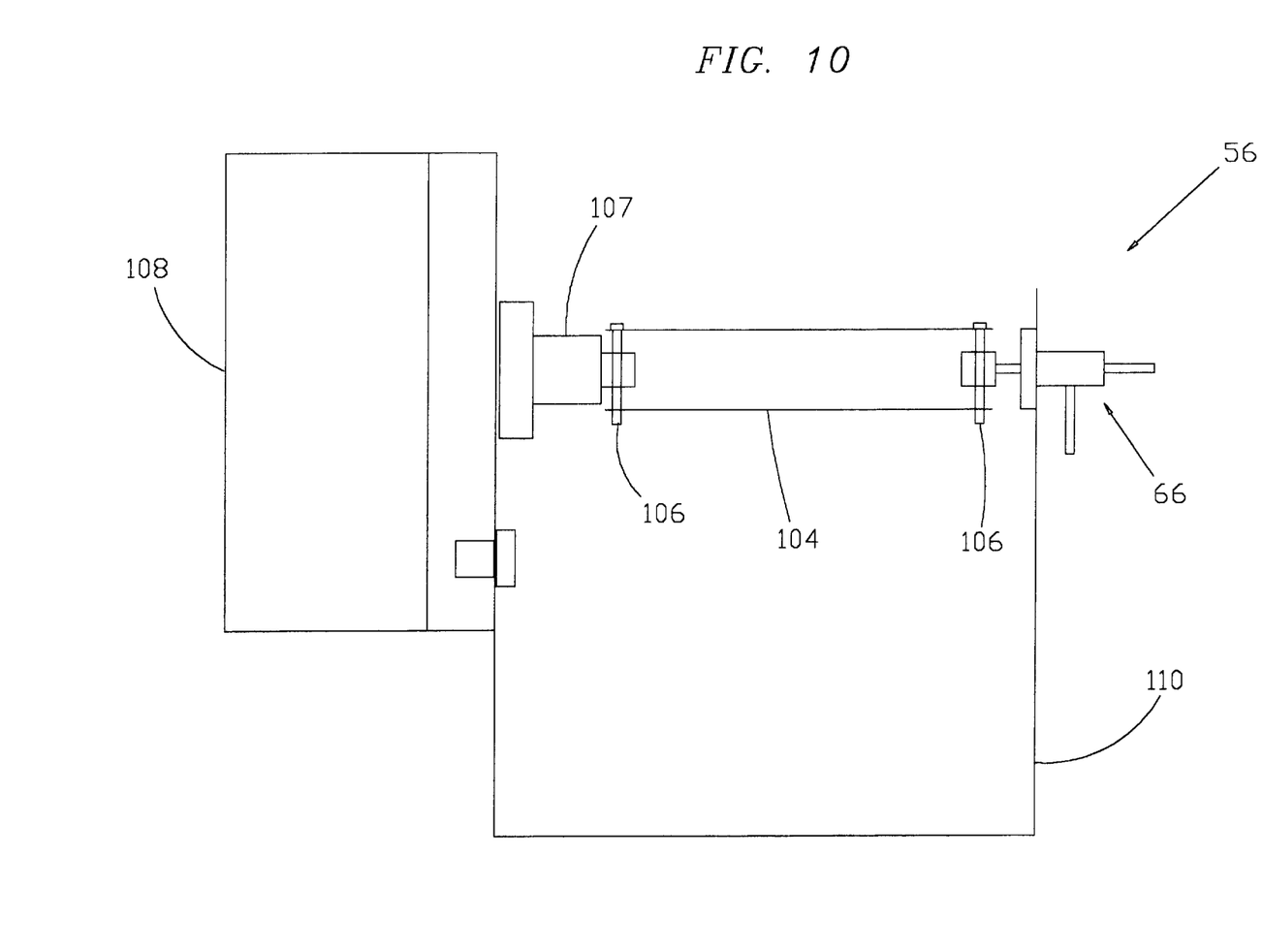
FIG. 10 is a side elevation view of a vacuum controller of the pollen preservation apparatus of FIG. 1.

FIG. 10 shows a detailed view of the vacuum control motor 56 of the vacuum controller 22. The vacuum control motor 56 is a general-purpose gear reduced service motor of the kind used, for example, for model airplanes. The vacuum control motor 56 is modified to allow the motor to continuously rotate through removal of the internal gear stops. The vacuum control motor 56 comprises a gear box 108 which rotates a shaft 107 connected to tubing 104 (quarter-inch Tygon tubing). Cable ties 106 secure the tubing to the motor shaft 107 on one end and to the second valve 66 on the other end. The second valve 66, like the first valve 60, comprises a needle valve of the type well-known in the art. Accordingly, the gear box 108 rotates the tubing 104 through its connection to the shaft 107 through cable ties 106, this in turn adjusts the position of the second valve 66 to regulate the amount of air flow that passes between the air source 28 and the vacuum manifold 38 along the second vacuum manifold path 62. Additionally, a mounting bracket 110 secures the vacuum control motor 56 to the vacuum controller 22 of the central controller 16.

Figure 4:
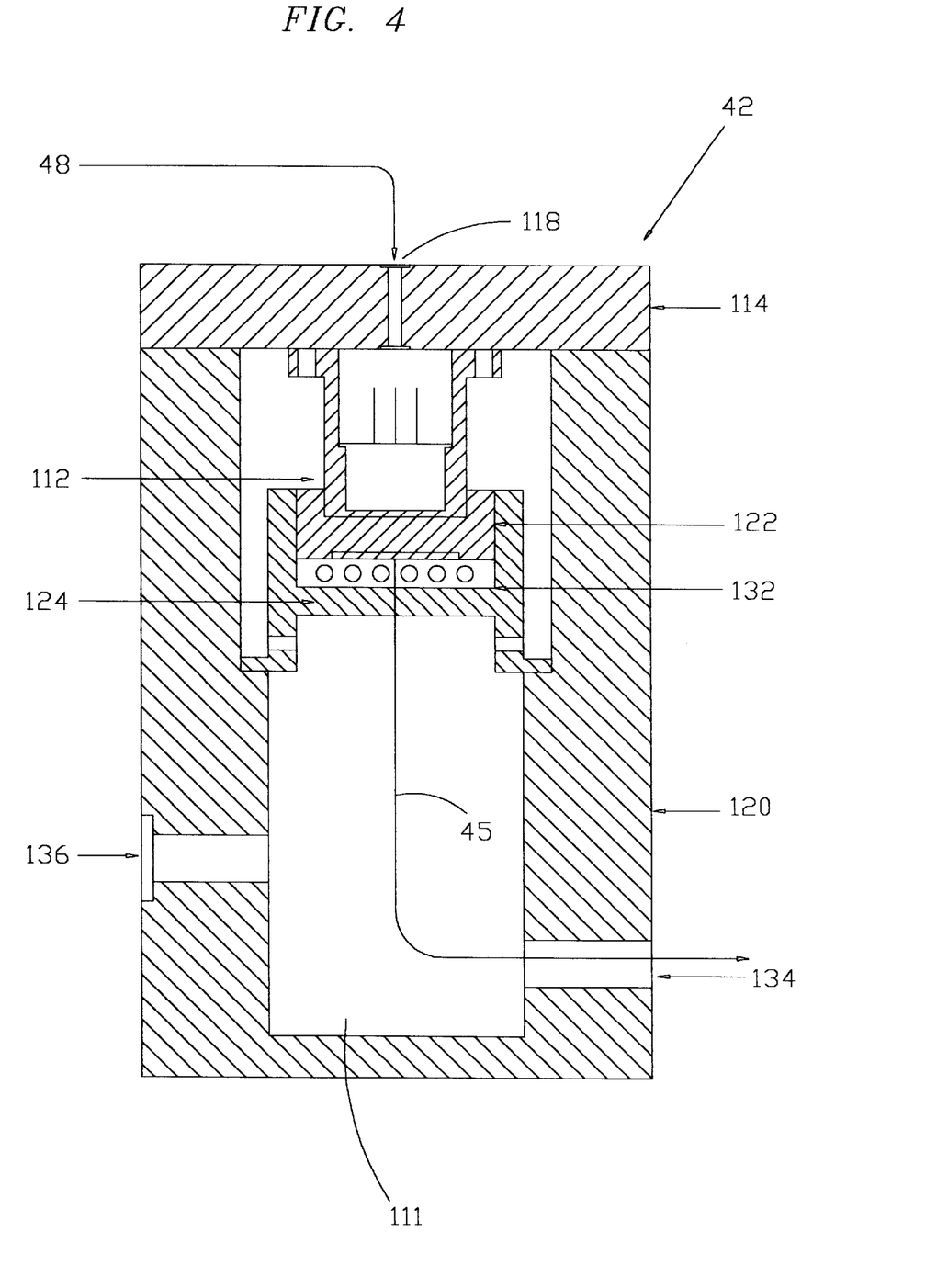
FIG. 4 is a cross-sectional view of the a chamber of the pollen preservation apparatus of FIG. 1.

FIG. 4 shows a cross-sectional view of one of the plurality of chambers 42. The chamber 42 is constructed from standard aluminum alloy (T6061) with no surface finish. The chamber 42 includes a temperature sensor 112 located within a chamber interior 111. The sensor 112 consists of a thermopile element that senses the temperature based on an established relationship between black body emissions and an object's temperature. The sensor 112, preferably an infrared type sensor, mounts to a removable lid 114. A sensor communication line 48 mounts to the removable lid 114 where the sensor communication line 48 passes through vacuum feedthroughs 118. The sensor communication line 48 provides operative communication between the sensor 112 and the central controller 16. The sensor 112 is adapted to be press fitted with the upper rim of the chamber 42 for optimum thermal contact. A single O-ring provides the vacuum seal between the removable lid 114 and a chamber body 120 of the chamber 42. A sample receptor 122 is positioned on a mechanically rigid platform 124. Also located within the chamber interior 111 is an oscillation element 132, in the preferred embodiment the oscillation element 132 comprises a piezo electric element. The oscillation element 132 operatively communicates with the oscillation controller 24 via the oscillation communication line 45 which passes through oscillation wire port 134 of the chamber body 120. A vacuum port 136 is designed to receive a vacuum line to allow for operative communication between the interior 111 of the chamber 42 and the vacuum controller 22. The vacuum port 136 is located within the chamber body 120 below the level of the sample holder 122. The sample holder 122 is a small aluminum cuvette adapted to maintain the pollen therein, and is of a shape that avoids sample scatter during evacuation and venting of the interior 111 of the chamber 42.

The aluminum construction of the chamber 42, and particularly the sample receptor 122 and the platform 124, proves important to the proper functioning of the invention. This construction facilitates vibration by minimizing dampening that can occur with the use of plastic or rubber to isolate the sample holder 122. Because the chamber 42 is composed of aluminum, the evaporating sample is able to easily draw heat from the surrounding material. This has the effect of regulating the temperature of the sample and preventing the formation of destructive ice crystals. The formation of ice crystals can result from too rapid of a cool down during the pressure cycle, and will reduce the viability of the pollen samples. The pressure step size and range used in the system, while necessary, would damage the sample through ice crystal formation if not for the ability to draw heat from the surrounding material. Also, because of the good thermal conductivity and high thermal mass of the sample holder and surrounding material, the energy loss to the sample does not significantly change the temperature of the sample holder 122 and surroundings. The temperature sensor 112 used for detecting the sample temperature is a relative sensor in that temperature of the sensor 112 is a factor in the perceived sample temperature. If the sample holder 122 temperature were to differ greatly from the temperature of the sensor 112, through the action of sample energy loss, then a time shift and amplitude distortion would be introduced into the important delta point value. While these distortions could be corrected for, the construction of the chamber 42 avoids the need to do so.

Figure 5:
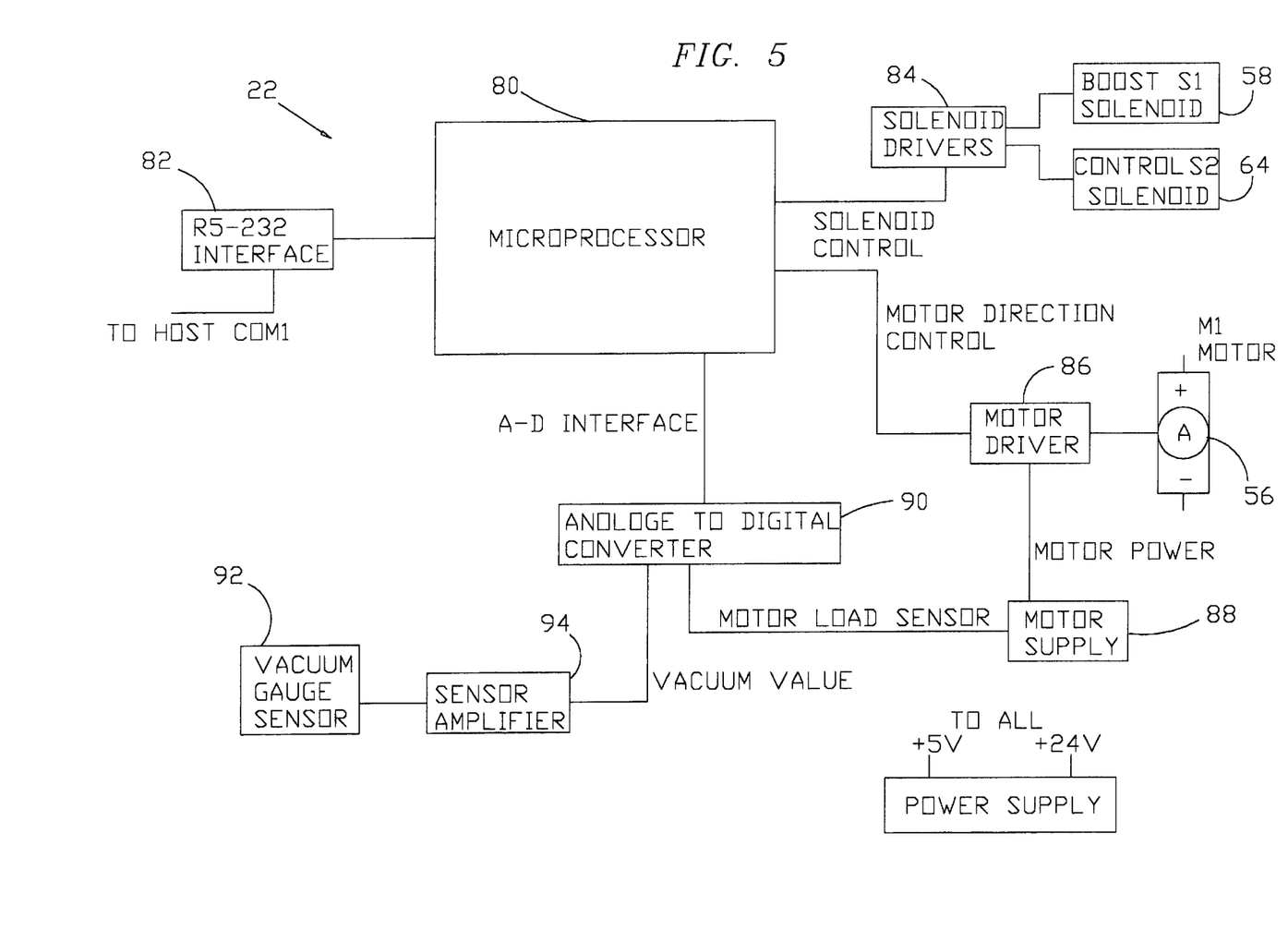
FIG. 5 is a block diagram of the vacuum controller of FIG. 2.

FIG. 5 shows a block diagram of the electrical system of the vacuum controller 22. A dedicated micro-controller unit 80 contains necessary program information for vacuum regulation and communication with the PC controller 18. Interface between the two computing units is done via serial protocol using standard RS-232 level signals. RS-232 signal levels are converted to levels useable by the micro-controller unit 80 via an RS-232 interface circuit 82. Vacuum regulation is achieved via a combination of first (boost) solenoid 58, second (control) solenoid 64, and the needle valve 66 and motor 56 assembly (shown in detail in FIG. 10). Signals to control these devices originate from the micro-controller unit 80. These signals must be amplified to properly control the vacuum components. The solenoid driver 84 boosts control signals going to the boost solenoid 58 and the control solenoid 64. Proper conditioning of motor control signals is done in the motor driver circuit 86. Power to drive the motor is provided by the motor supply circuit 88. The motor supply circuit 88 has two other important functions. First, it limits motor power to prevent damage to needle valve 66 that could occur under end of range conditions. Second, the motor supply circuit 88 senses the status of the needle valve 66 through a measure of motor load in the form of drive current is output to the Analog to Digital converter 90. System vacuum level is sensed via a vacuum gauge sensor 92 that is a solid state pressure transducer. A sensor amplifier 94 boosts the signal from the vacuum gauge sensor 92 to provide best possible resolution at pressure below 50 torr. The Analog to Digital converter 90 provides the micro-controller unit 80 with a numerical representation of physical information such as line vacuum from the vacuum gauge sensor 92 and the motor load sense from the motor supply 88.

Figure 6:
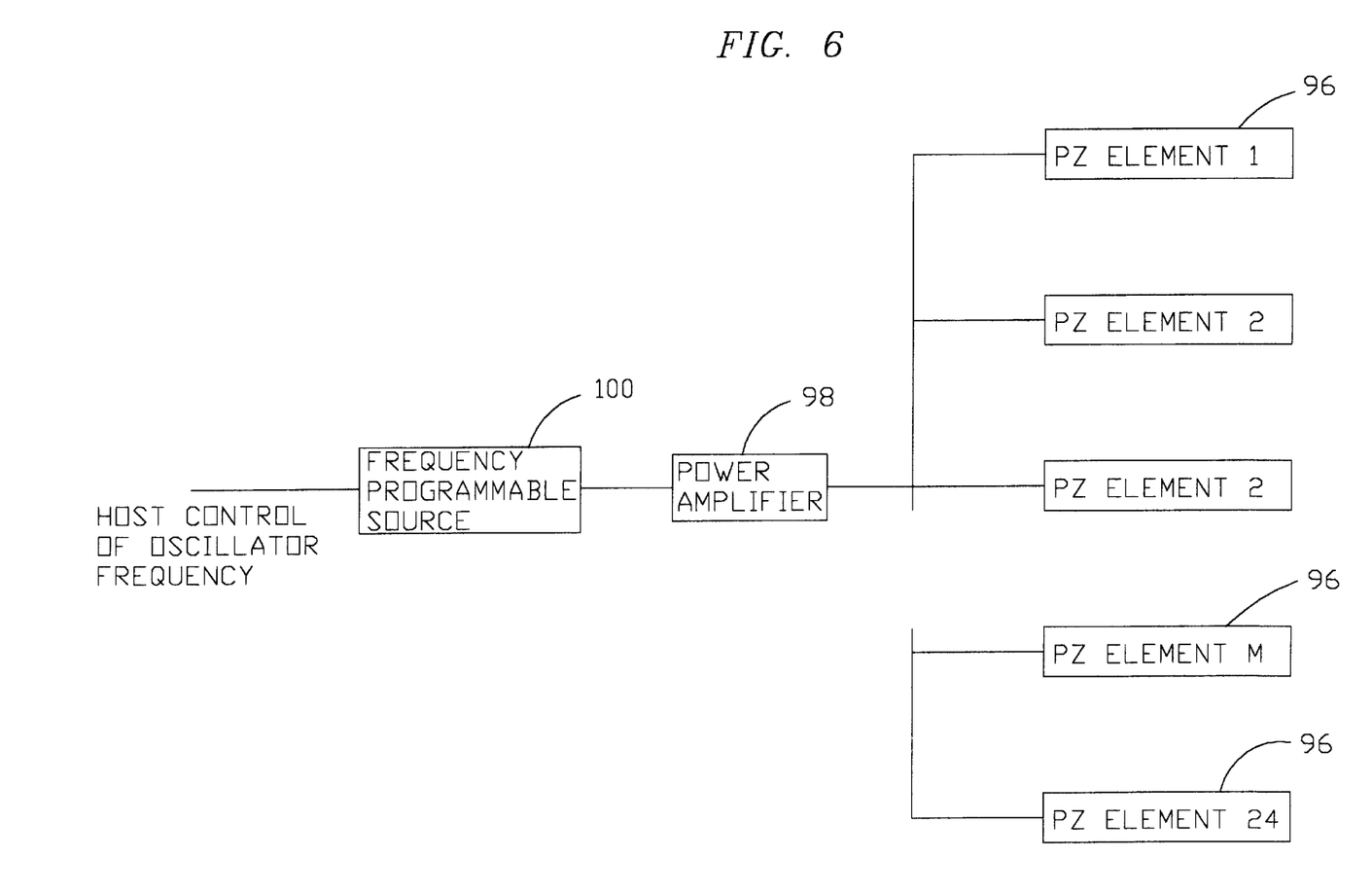
FIG. 6 is a block diagram of an oscillation controller of the pollen preservation apparatus of FIG. 1.

FIG. 6 shows schematically the oscillation control flow. The oscillation controller 24 comprises a frequency programmable source 100 and a power amplifier 98 which communicate through host control to the central controller 16. Also, the oscillation controller 24 operatively communicates over the oscillation communication line 45 with the plurality of oscillation elements 132. FIG. 6 depicts piezoelectric oscillation elements 96 which in the preferred embodiment of the present invention are the oscillation elements 132. The configuration in FIG. 6 requires that all of the piezoelectric elements 96 vibrate at the same frequency. However, due to subtle variations in the size, shape, weight of the plurality of chambers 42 not all of the chambers 42 resonate at exactly the same frequency. Accordingly, the frequency emanating from the frequency programmable source 100 varies cyclically in order to insure that the pollen samples in each of the plurality of chambers 42 vibrates sufficiently to prevent clumping of the pollen samples. Clumping if it occurs during sample preparation can seriously affect the reliability of pollen cryogenic preservation. Physical contact between the pollen grains causes this effect. Experimental results show that these points of physical contact between the pollen grains cause insufficient and an erratic drying of the pollen samples. During freezing these areas of contact form destructive ice crystals that interfere with the viability of the pollen. Because these areas of contact are not in-line with the sensor 112 the standard end of test conditions can be met before the pollen sample reaches a uniform moisture content level. Accordingly, the piezoelectric elements 96 are glued to the bottom of each sample receptor 122. The power amplifier 98 drives the piezoelectric elements 96 at such a frequency that a resonance is periodically set up within the chambers 42. As a result, in the preferred embodiment of the present invention, the oscillation frequency varies from a first frequency level of about 20 kHz and a second frequency level of about 25.4 kHz. At resonance the pollen grains move about energetically preventing the contact that will cause clumping during the drying process.

Figure 7:
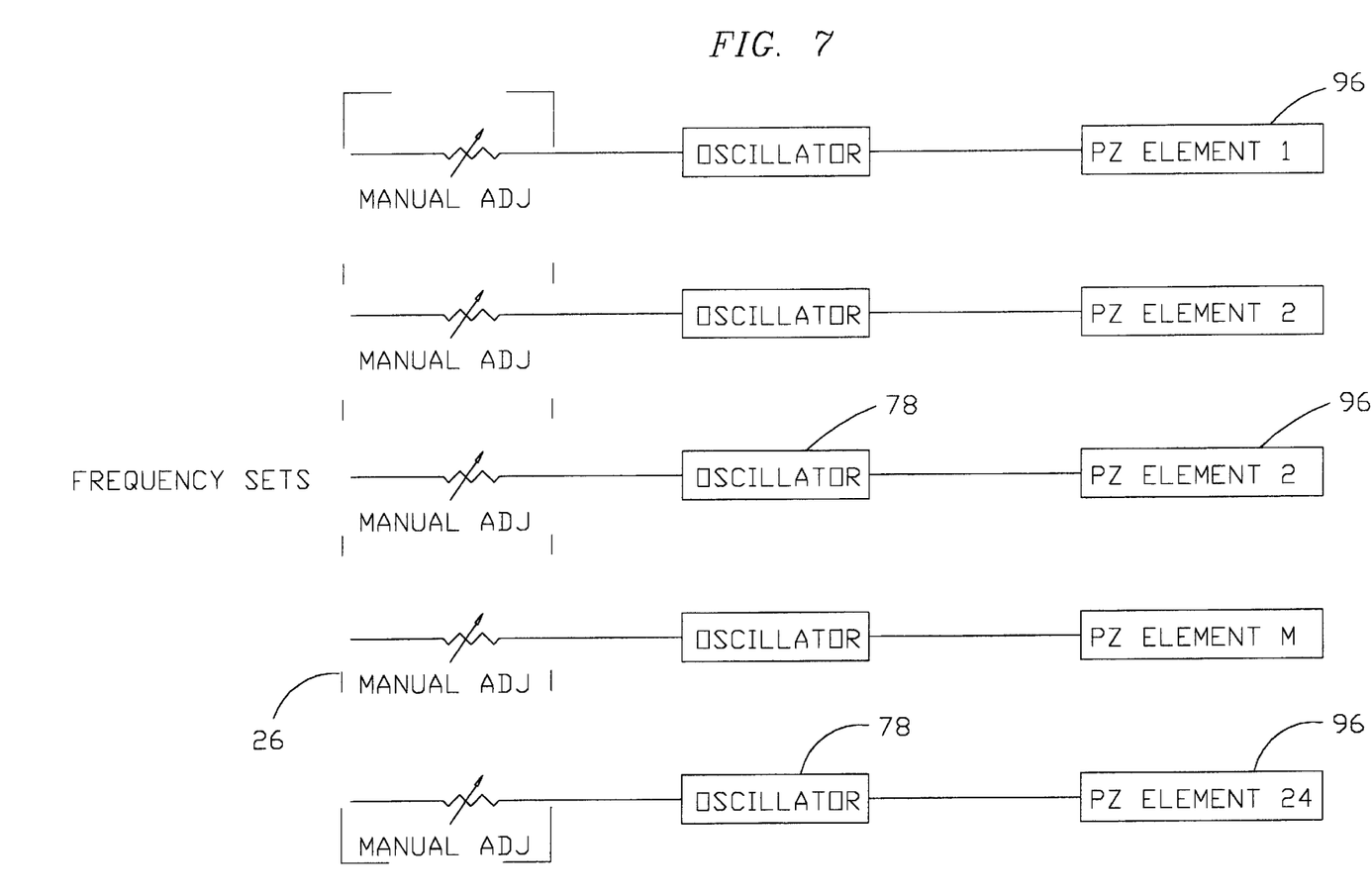
FIG. 7 is a block diagram of an alternative oscillation controller of the pollen preservation apparatus of FIG. 1.
Figure 8:
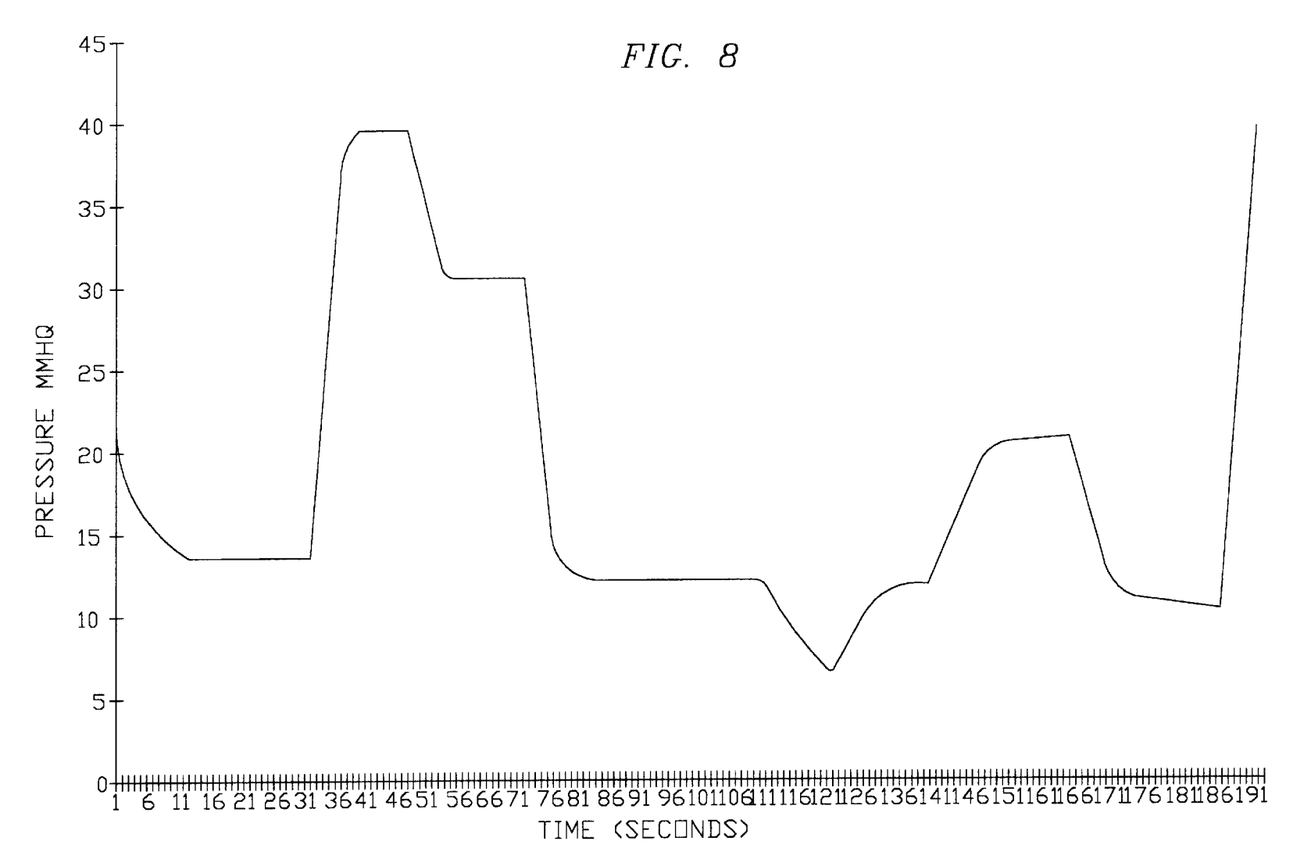
FIG. 8 is a graphical representation of the pressure within the interior of a plurality of chamber versus time.
Figure 9:
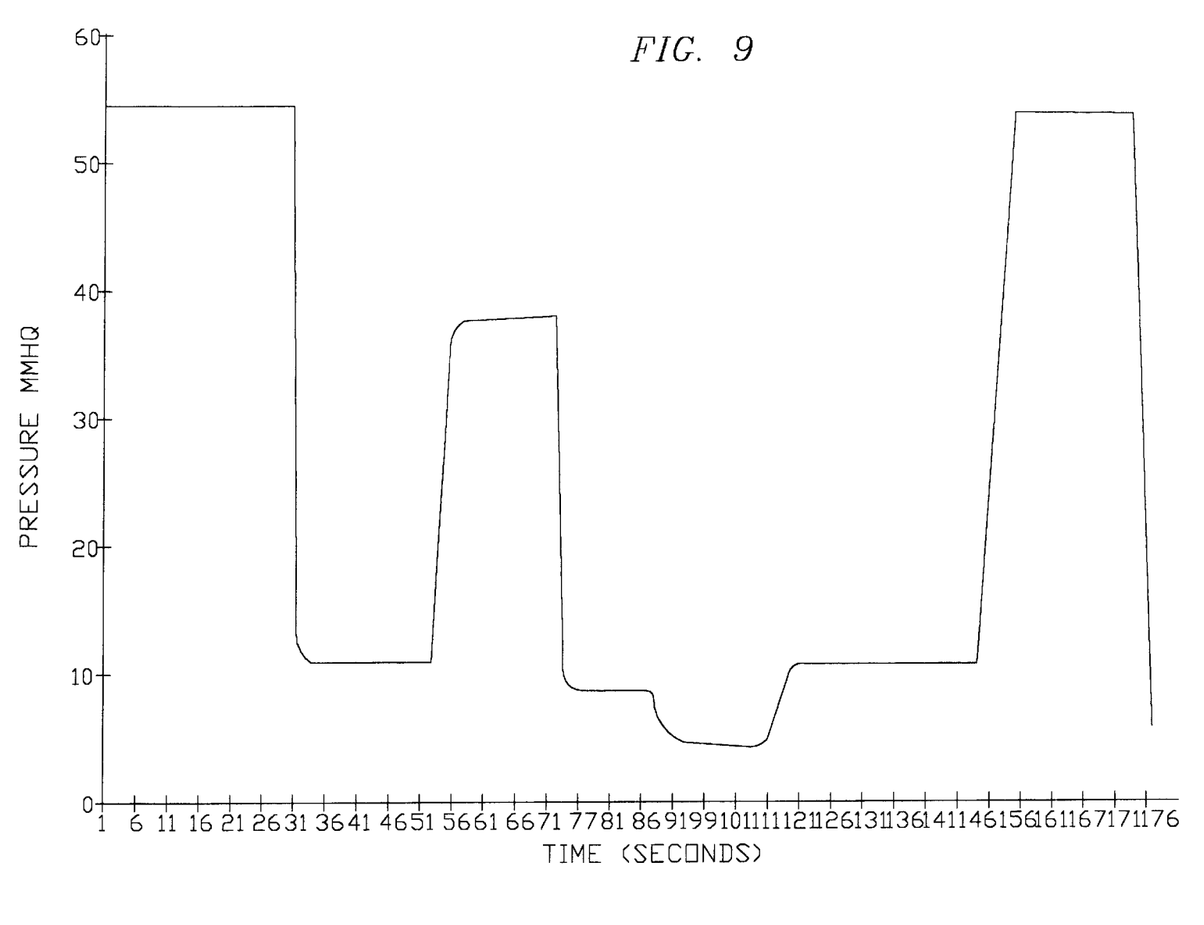
FIG. 9 is a graphical representation of the pressure within the interior of a single chamber versus time.

The oscillation method of the present invention proves superior to other oscillation methods. For example, electromagnetic means to oscillate the pollen samples proved less effective. The relatively large thermal mass required for the sample receptor 122, necessary to facilitate evaporation, would require a large amount of power to enable sufficient oscillation in the pollen sample. Large amounts of power in the chambers 42 creates excessive thermal and electromagnetic noise that can interfere with the relatively small signal coming from the sensor 112. FIG. 7 shows an alternative embodiment that allows for separate control of the oscillation frequency to each of the plurality of chambers 42. FIG. 7 shows a plurality of piezoelectric elements 96 each in operative communication with a separate oscillator 78, which in turn communicates with a separate manual oscillation frequency dial 26. The configuration shown in FIG. 7 allows for separately tuning the resonant frequency of each of the plurality of chambers 42. This eliminates the need to vary the frequency, but this method has the drawback of requiring substantially more components, and more setup effort.

The following describes the operation of the pollen preparation apparatus 10. In particular, operation of the pollen preparation apparatus 10 begins with the operator bringing on-line at least one of the plurality of chambers 42. The operator accomplishes this task by selecting the particular chambers 42 and then communicating that information to the system controller 16 via the keyboard 32. The system is capable of bringing on-line any combination of the plurality of chambers 42 at any time during the processing cycle. Selecting a particular chamber 42 simply requires opening the chamber solenoid 76 for that particular chamber 42, which will open air flow between the chamber 42 and the first and second vacuum manifold paths 54, 62 and the vacuum path 55. Additionally, the chamber solenoid 76 for the particular chamber 42 that allows air flow between the chamber 42 and the air manifold path 72 is closed. With the chamber solenoids 76 set in this position the chamber 42 is on line and the pressure within the interior 111 of the chamber 42 comes under control of the vacuum controller 22. To bring any other chamber 42 on-line simply requires placing the chamber solenoids 76 for that particular chamber 42 in the previously described configuration. Taking a chamber off-line, conversely, merely requires reversing the position of the chamber solenoids 76 for that particular chamber 42.

After selecting the appropriate chambers 42, process control switches to the vacuum controller 22. In order to begin operation, the vacuum controller 22 closes the first solenoid 58 and the second solenoid 64. This prevents any air flow communication between the air source 28 and the vacuum manifold 38. At this point the vacuum pump 12 engages thereby evacuating the vacuum path 55. This creates a vacuum in each of the on-line chambers 42. With the first solenoid 58 and the second solenoid 62 closed the vacuum controller pumps down the chambers 42 in a rapid pump-down phase. The rapid pump-down phase continues until the vacuum gauge 68 signals that the pressure has reached approximately 10% of a first reduced pressure level. In the preferred embodiment of the present invention the first reduced pressure level equals about 20 torr. Upon reaching approximately 10% of the first reduced pressure level the system enters vacuum regulation mode. In vacuum regulation mode, the first solenoid 58 remains closed while the second solenoid 64 opens to allow variable air flow between the air source 28 and the vacuum manifold 38. This allows the vacuum control motor 56 to regulate the pressure. In other words, with the second solenoid 64 open the vacuum control motor 56 can manipulate the position of the second valve 66 to control the amount of air moving from the air source 28 into the vacuum path 55. The vacuum controller 22 through manipulating the vacuum control motor 56 holds the pressure at the first reduced pressure level thereby beginning the first of a series of pressure cycles.

Figure 11:
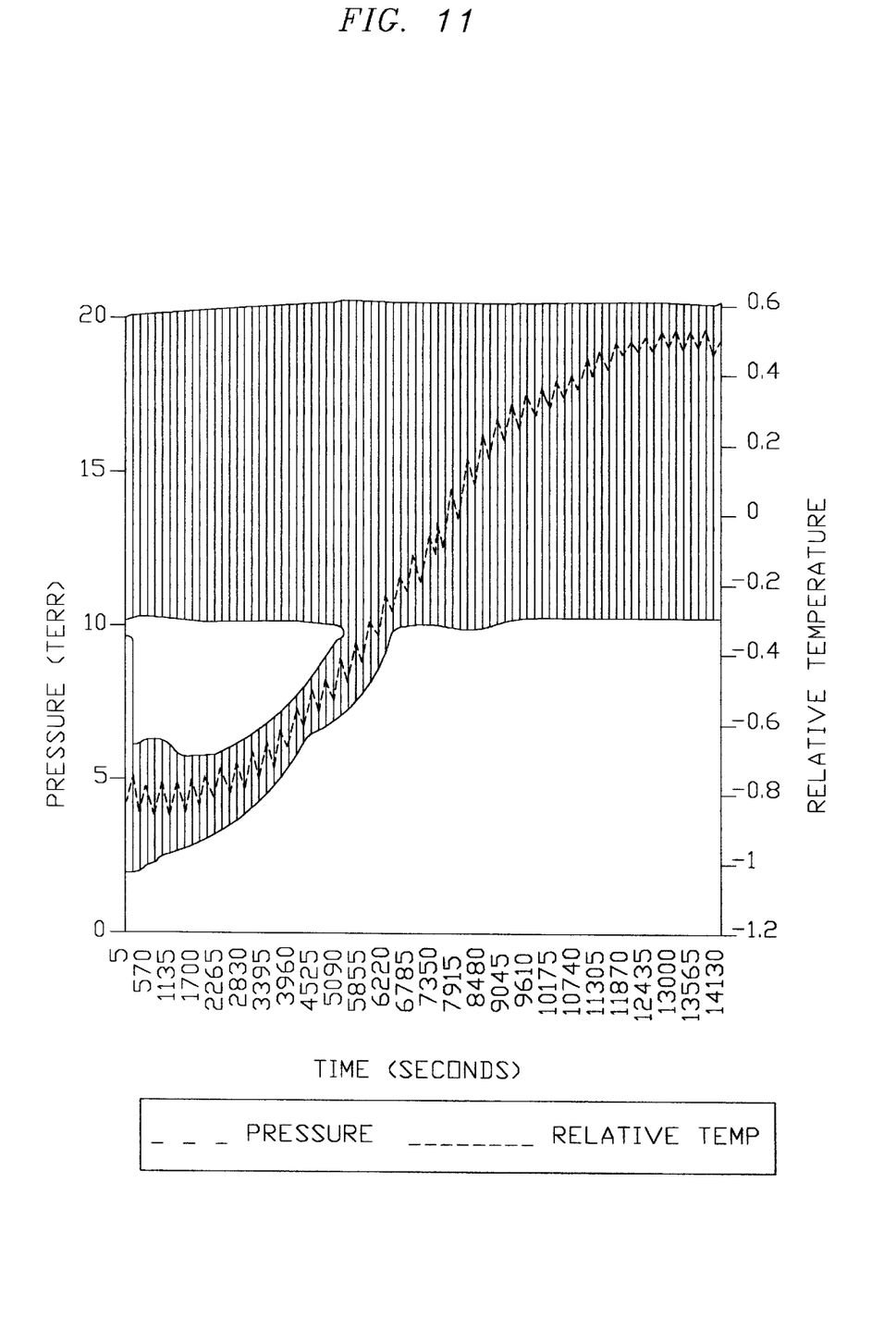
FIG. 11 is a graphical representation of the pressure/relative temperature within the interior of a chamber versus time.

In the preferred embodiment of the present invention the pressure cycle consists of a period of about 120 seconds. During the pressure cycle the pressure is maintained at the first reduced pressure level for about 105 seconds, and then the pressure is maintained at a second reduced pressure level for about 15 seconds. In the preferred embodiment of the present invention the second reduced pressure level equals about 12 torr. Thus, after maintaining the pressure at the first reduced pressure level for about 105 seconds, the vacuum controller 22 manipulates the vacuum control motor 56 to set the second valve 66 in a position that reduces the amount of air flowing from the air source 28 into the vacuum path 55 until the vacuum gauge 68 registers the second reduced pressure level. In other words, the vacuum controller 22 pulses (or ramps) the pressure between the first reduced pressure level and the second reduced pressure level on a periodic basis. The pulsing of the pressure proves important for two reasons. First, pulsing the pressure speeds up the evaporation process. In some cases pulsing can decrease the cycle time by one hour to one and a half hours. Second, pulsing the pressure actually allows the central controller 16 to determine in absolute terms a moisture content level. The combination of reduced pressure and pulsing pressure causes water to evaporate from the pollen sample. This drop in moisture content level causes a corresponding temperature change in the pollen sample. The infrared temperature sensor 112 registers the changes in temperature level of the pollen sample within the interior 111 of the chamber 42. In particular, the difference between the relative temperatures at the first reduced pressure level and the second reduced pressure level within a particular pressure cycle, commonly called the delta point, allows for direct estimation of an absolute moisture content level of the pollen sample. FIG. 11 demonstrates the effect of pressure pulsing treatment on a pollen sample, as evidenced by the change in the infrared signal from a pollen sample over a four-hour drying period. Clearly, the delta points associated with the infrared pulses of each pressure cycle decline in magnitude over time, and the traces begin to reach a plateau sometime after the three-hour point. Thus, through a signaling means operatively connected to the sensor 112 the central controller 16 can sense a predetermined moisture content level, at which point the pollen preparation apparatus 10 can terminate the preparation of the pollen sample within any particular chamber 42. According to the methods of the present invention, and in particular reference to maize pollen, a pre-determined moisture content level of between about 8% and about 10% moisture content by weight proves adequate to support viability of maize pollen for the purposes of cryogenic preservation. Those of ordinary skill in the art will appreciate the availability of other methods and means for sensing the moisture content level of pollen samples without departing from the intended scope of the present invention.

The pollen preparation apparatus 10 allows an operator at any time during the operation of the apparatus 10 to take a chamber 42 off-line, or bring an additional chamber 42 on-line without interrupting the operation of any of the other chambers 42. For example, to bring an additional chamber 42 on-line during the operation of the apparatus 10, the operator merely selects the particular chamber 42 from the keyboard 32 transmitting the information to the central controller 16. At this point, the central controller causes the chamber solenoid 76 for the particular chamber 42 to close air flow between the chamber 42 and the air manifold path 72, and opens air flow between the chamber 42 and the first and second vacuum manifold paths 54, 62 and the vacuum path 55. With the vacuum path 55 already at a reduced pressure level, the pressure within the interior 111 of the newly engaged chamber 42 drops to the reduced vacuum level. Generally, the chamber 42 begins to pump down within 5 seconds of selection of the chamber 42. The chamber 42 then drops into the pressure cycle with the rest of the on-line chambers 42. To take a chamber 42 off-line during the operation of the pollen preparation apparatus 10 merely involves closing the chamber solenoid 76 which controls the air flow between the chamber 42 and the first and second vacuum manifold paths 54, 62, and the vacuum path 55 and opening the chamber solenoid 76 which controls the air flow between the chamber 42 and the air manifold path 72. Configured in this manner air can now flow from the air source 28 to the chamber 42 along the air manifold path 72 venting the chamber 42 to atmosphere without interfering with the operation of any of the other chambers 42 under vacuum.

Upon termination of the operation of the pollen preparation apparatus 10, and/or in an effort to rapidly vent all the chambers 42 the system enters pressure step boost mode. In pressure step boost mode the first solenoid 58 and the second solenoid 64 configure to the open position and the vacuum pump 55 disengages thereby allowing maximum air flow through the vacuum controller from the air source 28 to the vacuum manifold 38. An alternative method to vent the vacuum circuits for shutdown comprises opening the first solenoid 58 and closing the second solenoid 64. This enables air to flow from the air source 28 through the vacuum controller 22 to the vacuum manifold 38.

FIGS. 8–9 show pressure response curves over time for two separate configurations of on-line chamber arrangements, which demonstrate the minimum pressure pulse duration. FIG. 8 shows the response over time with all twenty-four chambers 42 on-line. FIG. 8, therefore, shows the worst case scenario for the time required for the pressure to level off, or plateau. By contrast, FIG. 9 shows the pressure versus time response for one chamber 42 on line. Accordingly, duration of the pressure pulses should be set to allow the pressure plateau to level off based on the worst case pressure scenario shown in FIG. 8.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the

What is claimed is:

1. An apparatus for the preparation of multiple pollen samples for cryogenic preservation, said apparatus comprising:
    a) a plurality of chambers wherein each of said chambers has an interior for storing the pollen samples;
    b) a vacuum manifold operatively connected to said chambers for reducing the pressure of said interiors of said chambers;
    c) an air manifold operatively connected to said chambers for venting said interiors of said chambers to atmospheric pressure;
    d) a vacuum pump;
    e) an air source at atmospheric pressure;
    f) a vacuum controller operatively connected to said vacuum manifold, to said air manifold, to said air source, and to said vacuum pump for controlling said pressure within said interiors of said chambers such that said pressure is pulsed between a first reduced pressure level and a second reduced pressure level; and
    g) a sensor operatively connected to said plurality of chambers for sensing the moisture content of the pollen samples within said interior of said plurality of chambers at said reduced pressure levels.

2. The invention in accordance with claim 1 further comprising an oscillation controller operatively connected to an oscillation element located within said interiors of said chambers wherein said oscillation controller causes said oscillation element to vibrate thereby vibrating the pollen samples.

3. The invention in accordance with claim 2 wherein said oscillation element comprises a piezo electric element.

4. The invention in accordance with claim 2 wherein said oscillation controller varies said vibration by pulsing an oscillation frequency between a first frequency level and a second frequency level.

5. The invention in accordance with claim 4 wherein said first frequency level is about 20 kHz and said second frequency level is about 25.4 kHz.

6. The invention in accordance with claim 2 further comprising a plurality of oscillation controllers wherein each of said plurality of chambers has a separate oscillation controller.

7. The invention in accordance with claim 1 wherein said first reduced pressure level is about 20 torr and said second reduced pressure level is about 12 torr.

8. The invention in accordance with claim 1 wherein said vacuum controller controls said first and said second reduced pressure levels according to a pressure cycle.

9. The invention in accordance with claim 8 wherein said pressure cycle is about 120 seconds in length.

10. The invention in accordance with claim 9 wherein said first reduced pressure level is maintained for about 105 seconds, and said second reduced pressure level is maintained for about 15 seconds.

11. The invention in accordance with claim 1 wherein said vacuum controller further comprises:
    a) a vacuum path for air flow communication between said vacuum pump and said vacuum manifold, said vacuum path comprising a vacuum gauge for monitoring said pressure;
    b) a first vacuum manifold path comprising a first solenoid located in series with, a first valve, said vacuum manifold, and said air source wherein said first solenoid opens and closes air flow along said first vacuum manifold path, and said first valve regulates air flow between said air source and said vacuum manifold;
    c) a second vacuum manifold path parallel to said first vacuum manifold path comprising a vacuum control motor located in series with a second solenoid, a second valve, said vacuum manifold, and said air source wherein operation of said motor pulses said pressure between said first reduced pressure level and said second reduced pressure level by varying the position of said second valve thereby regulating air flow between said air source and said vacuum manifold, and wherein said second solenoid opens and closes air flow along said second vacuum manifold path; and
    d) an air manifold path comprising a third valve for regulating the air flow between said air source and said air manifold.

12. The invention in accordance with claim 11 wherein said vacuum manifold comprises a plurality of chamber solenoids such that each of said chamber solenoids open and close air flow between one of said plurality of chambers and said first and second vacuum manifold paths and said vacuum path of said vacuum controller.

13. The invention in accordance with claim 11 wherein said air manifold comprises a plurality of chamber solenoids such that each of said chamber solenoids open and close air flow between one of said plurality of chambers and said air manifold path of said vacuum controller.

14. The invention in accordance with claim 1 wherein the pollen samples comprise maize pollen.

15. The invention in accordance with claim 1 wherein the pollen samples comprise wheat pollen.

16. The invention in accordance with claim 1 wherein the pollen samples comprise barely pollen.

17. The invention in accordance with claim 1 wherein the pollen samples comprise sorghum pollen.

18. The invention in accordance with claim 1 further comprising a signaling means operatively connected to said sensor for signaling that said sensor has sensed a predetermined moisture content level.

19. The invention in accordance with claim 18 wherein said predetermined moisture content level is between about 8% and about 10% moisture content by weight.

20. The invention in accordance with claim 1 wherein said sensor comprises a heat sensor.

21. The invention in accordance with claim 20 wherein said heat sensor is an infrared sensor.

22. The invention in accordance with claim 1 wherein said plurality of chambers are comprised of aluminum.

23. An apparatus for the preparation of multiple corn pollen samples for cryogenic preservation, said apparatus comprising:
    a) a plurality of chambers comprised of aluminum wherein each of said chambers has an interior for storing the corn pollen samples;
    b) a vacuum manifold operatively connected to said chambers for reducing the pressure of said interiors of said chambers, said vacuum manifold comprising a plurality of chamber solenoids;
    c) an air manifold operatively connected to said chambers for venting said interiors of said chambers to atmospheric pressure, said air manifold comprising a plurality of chamber solenoids;
    d) a vacuum pump;
    e) an air source at atmospheric pressure;

f) a vacuum controller operatively connected to said vacuum manifold, to said air manifold, to said air source, and to said vacuum pump for controlling said pressure within said interiors of said chambers such that said pressure is pulsed between a first reduced pressure level of about 20 torr and a second reduced pressure level of about 12 torr according to a pressure cycle of about 120 seconds wherein said first reduced pressure level is maintained for about 105 seconds, and said second reduced pressure level is maintained for about 15 seconds, said vacuum controller comprising:
  i) a vacuum path for air flow communication between said vacuum pump and said vacuum manifold, said vacuum path comprising a vacuum gauge for monitoring said pressure;
  ii) a first vacuum manifold path comprising a first solenoid located in series with, a first valve, said vacuum manifold, and said air source wherein said first solenoid opens and closes air flow along said first vacuum manifold path, and said first valve regulates air flow between said air source and said vacuum manifold;
  iii) a second vacuum manifold path parallel to said first vacuum manifold path comprising a vacuum control motor located in series with a second solenoid, a second valve, said vacuum manifold, and said air source wherein operation of said motor pulses said pressure between said first reduced pressure level and said second reduced pressure level by varying the position of said second valve thereby regulating air flow between said air source and said vacuum manifold, and wherein said second solenoid opens and closes air flow along said second vacuum manifold path;
  iv) an air manifold path comprising a third valve for regulating the air flow between said air source and said air manifold; and
  v) whereby said chamber solenoids of said vacuum manifold open and close airflow between one of said plurality of chambers and said first and second vacuum manifold paths, said vacuum path, and said air manifold path.

g) a infrared heat sensor operatively connected to said plurality of chambers f or sensing the moisture content of the pollen samples within said interior of said plurality of chambers at said reduced pressure levels;

h) a plurality of oscillation controllers operatively connected to a plurality of piezo electric oscillation elements located within said interiors of said chambers wherein said oscillation controller causes said oscillation element to vibrate thereby vibrating the pollen samples, whereby said oscillation controllers varies said vibration by varying an oscillation frequency between a first frequency level of about 20 kHz and a second frequency level of about 25.4 kHz; and i) signaling means operatively connected to said sensor for signaling that said sensor has sensed a predetermined moisture content level of between about 8% and about 10% moisture content by weight.

* * * * *